United States Patent [19]

Ikeda et al.

[11] Patent Number: 5,763,497
[45] Date of Patent: Jun. 9, 1998

[54] OIL-IN-WATER TYPE COSMETIC COMPOSITION

[75] Inventors: Tomoko Ikeda; Masanori Aizawa, both of Yokohama, Japan

[73] Assignee: Shiseido Company, Ltd., Tokyo, Japan

[21] Appl. No.: 647,983

[22] PCT Filed: Jul. 20, 1995

[86] PCT No.: PCT/JP95/01445

§ 371 Date: May 31, 1996

§ 102(e) Date: May 31, 1996

[87] PCT Pub. No.: WO96/03107

PCT Pub. Date: Feb. 8, 1996

[30] Foreign Application Priority Data

| Jul. 21, 1994 | [JP] | Japan | 6-190997 |
| Jul. 21, 1994 | [JP] | Japan | 6-190998 |
| Mar. 31, 1995 | [JP] | Japan | 7-100545 |

[51] Int. Cl.⁶ .................................... A01N 43/80
[52] U.S. Cl. ................... 514/943; 424/69; 424/78.02; 424/78.03; 424/489; 514/937; 514/938
[58] Field of Search .................. 424/401, 78.02, 424/78.03, 69, 489; 514/937, 938, 943

[56] References Cited

U.S. PATENT DOCUMENTS

| 4,871,536 | 10/1989 | Arraudeau et al. | 424/59 |
| 5,053,222 | 10/1991 | Takasu et al. | 424/7 |
| 5,068,101 | 11/1991 | Akhtar et al. | 424/71 |
| 5,071,640 | 12/1991 | Vanlerberghe et al. | 424/63 |
| 5,077,042 | 12/1991 | Darkwa et al. | 424/71 |
| 5,100,655 | 3/1992 | Takano et al. | 424/63 |
| 5,153,340 | 10/1992 | Ichikawa et al. | 552/509 |
| 5,160,730 | 11/1992 | Dubief et al. | 424/59 |
| 5,171,565 | 12/1992 | Akhtar et al. | 424/71 |
| 5,206,016 | 4/1993 | Orbán et al. | 424/401 |
| 5,344,650 | 9/1994 | Otsuka et al. | 424/401 |
| 5,419,896 | 5/1995 | Bimczok et al. | 424/74 |
| 5,474,778 | 12/1995 | Ichikawa et al. | 424/401 |
| 5,543,436 | 8/1996 | Hocquaux et al. | 424/61 |
| 5,554,362 | 9/1996 | Maresch et al. | 424/70.51 |
| 5,569,451 | 10/1996 | Richard et al. | 424/63 |
| 5,587,174 | 12/1996 | Lang et al. | 424/401 |

FOREIGN PATENT DOCUMENTS

| 57-171431 | 10/1982 | Japan . |
| 58-162510 | 9/1983 | Japan . |
| 63-150221 | 6/1988 | Japan . |
| 64-79104 | 3/1989 | Japan . |
| 3-166367 | 7/1991 | Japan . |
| 3-279319 | 12/1991 | Japan . |
| 5-178723 | 7/1993 | Japan . |
| 7-17828 | 1/1995 | Japan . |

*Primary Examiner*—Terressa Mosley
*Attorney, Agent, or Firm*—Wenderoth, Lind & Ponack, L.L.P.

[57] ABSTRACT

A composition which is one comprising water, a wax ester, and at least one of other components usable in cosmetics, and contains an ester composed of $C_{18-34}$ fatty acid—$C_{18-44}$ higher alcohol, and an amphoteric surface active agent, and can further contain a $C_{18-34}$ higher fatty acid.

It is possible to provide an intermediate composition for cosmetics and the above final product which are excellent in feelings in use to skin, and have physical and chemical characteristics for making their stable storage possible, and can be advantageously used particularly for foundation, lipstick, eye shadow, etc.

18 Claims, No Drawings

OIL-IN-WATER TYPE COSMETIC COMPOSITION

TECHNICAL FIELD

This invention relates to an oil-in-water type cosmetic composition, and more specifically, relates to an oil-in-water type solid composition fit for foundation, eye shadow, lipstick, etc.

BACKGROUND ART

As types of solid cosmetics which have so far generally been used, there are solid, oily types wherein an oil is solidified with a wax; solid, pressed types wherein a powder or a mixture of a powder and an oil is pressed; solid, water-in-oil type emulsification types which comprise a specific oil solidifying agent, a powder subjected to a treatment for making it hydrophobic, water, and a lipophilic surface active agent; etc., and they are used appropriately in accordance with the use objects and use methods of the respective cosmetics.

Among them, solid, water-in-oil type emulsification types are, particularly, good in stability and water resistance, and further have a wet use feeling, and one obtained by emulsifying a silicone oil, solid wax and water with a polyoxyalkylene-modified organopolysiloxane is known (Japanese Laid-open Patent Publication No. 79104/1989). However, since in these water-in-oil type emulsification types, the oil component and the oil solidifying agent are compounded in their outer phase, they are inferior to oil-in-water type milky lotions and creams in "being fresh-looking", "refreshed feeling" and "being free of stickiness".

Further, as an example of products obtained by solidifying an oil-in-water type emulsification type, one obtained by compounding a large amount of a higher alcohol or a clay mineral is known. However, in this oil-in-water type emulsification type, due to the above components compounded in a large amount, "being fresh-looking", "refreshed feeling" and "being free of stickiness", which oil-in-water type milky lotions and creams naturally have, are lost. As other examples of solid oil-in-water type emulsification types, there are known, for example, one obtained by solidifying water of the outer phase with a fatty acid soap (Japanese Laid-open Patent Publication No. 279319/1991), and one obtained by conducting solidification with combined use of a water soluble solidifying agent and a water soluble sticking agent (Japanese Laid-open Patent Publication No. 178723/1993 and Japanese Laid-open Patent Publication No. 17828/1995). However, as to the former, since its soap content is high, its pH becomes high, and therefore, there are problems on stimulation of skin and safety, and as to the latter, there are problems that sufficient hardness cannot be obtained, and it is hard to use with a sponge.

Further, as an emulsification technique developed in recent years, there is known a technique wherein a water insoluble composite is formed from an amphoteric surface active agent and a higher fatty acid, and emulsification stability is secured with this composite acting as an interfacial membrane for emulsification (Japanese Laid-open Patent Publication No. 166367/1991), but even by using this technique, it has been difficult to obtain a solid emulsification type, moreover "being fresh-looking", "refreshed feeling" and "being free of stickiness".

On the other hand, milky lotions and creams are generally fluid in the range of 0° C. to 50° C., and therefore, made into vessel forms of bottles or tubes, and a little inferior in the aspect of portability and easiness of use, and particularly in the case of foundation, the tendency has been conspicuous.

Under the above circumstances, it is the actual situation that a solid and emulsification composition is not obtained which is a solid and which is good in portability and easiness of use, and moreover, has use feelings of "being fresh-looking", "refreshed feeling" and "being free of stickiness" which milky lotions and creams have.

Thus, the object of the invention lies in providing a composition which exhibits use feelings of "being fresh-looking", "refreshed feeling" and "being free of stickiness" which oil-in-water type milky lotions and creams have, is excellent in portability and easiness of use, and can be used advantageously as a solid cosmetic.

DISCLOSURE OF INVENTION

The present inventors have made sequential researches for attaining the above object, and have found that a solid oil-in-water type emulsification composition excellent in stability and use feelings can be obtained by using a specific wax ester and an amphoteric surface active agent in combination, or by using both components further in combination with a higher fatty acid.

The thus obtained composition exhibits extremely excellent physical properties as mentioned above, although, for example, neither a water soluble solidifying agent nor a water soluble sticking agent, which is contained in usual oil-in-water type solid cosmetics, is used.

Thus, according to the invention, there is provided a cosmetic composition which is an oil-in-water type cosmetic composition comprising water, a wax ester and at least one of other components compounded in cosmetics, and contains, based on the total weight of the composition, (A) 0.1 to 10.0% by weight of at least one ax ester having a part derived from $C_{18-34}$ higher fatty acid and a part derived from $C_{18-44}$ higher fatty alcohol, and (B) 0.5 to 10.0% by weight of at least one amphoteric surface active agent.

Further, there is also provided a cosmetic composition comprising the above component (A) and component (B), and a definite amount of at least one $C_{6-34}$ higher fatty acid as a component (C).

Still further, there is also provided a solid cosmetic wherein at least one selected from the group consisting of a silicone oil, an ester oil (or a semi-solid wax ester), a higher alcohol, a water soluble macromolecule, a fatty acid ester of ethylene glycol or glycerol, titanium oxide and spherical powder, usable in the concerned technical field, is incorporated, as another component, in accordance with the object, in the above component (A) and component (B), or in the component (A), the component (B) and the component (C).

BEST MODE OF CARRYING OUT THE INVENTION

The term "solid" used in the invention means that the composition or component does not show fluidity at temperatures of 50° C. or less, and is in such a state that it does not show conspicuous deformation under usual, or even wrong use and storage conditions. Specifically, the term means that a desired amount thereof can be taken from the composition or component having a definite shape by use of a finger, a sponge, a puff or the like, and the residual part is in such a state that it has a hardness enough to maintain almost the original form.

More specifically, as to the hardness, it is required that when measured at 37° C. using a penetrometer (Reometer) usually used in the technical field concerned, hardness ($\gamma$) represented by the following formula is 7 or more.

$$\gamma \text{ (Hardness)} = \frac{G \times L}{l \times a} \text{ (dyn/cm}^2\text{)}$$

wherein,

G: Measured stress (gr)×980 dyn
L: Thickness of the sample (mm)
l: Compression distance (mm)
a: Cross section of the needle (cm$^2$)
(Measurement conditions)
Negative load: 2 kg
Diameter of needle: 5.6 $\phi$
Penetration speed: 2 cm/min
Penetration distance: 1 mm
Measurement temperature: 37° C.

On the other hand, for the object of the invention, it is preferred that a composition according to the invention has moderate fluidity at temperatures higher than 50° C. so that the respective components constituting it can be uniformly mixed or emulsified.

Although the present description is made, mainly with use of the composition of the invention as foundation in mind, it will also be easy for a person skilled in the art to choose another combination in accordance with the object, using the above hardness as an index. Therefore, the invention should not be limited by the following description.

The wax ester used in the invention is a carboxylic acid ester which is waxy at ordinary temperature, and composed of a part derived from a $C_{18-34}$ higher (or long-chain) fatty acid and a $C_{18-44}$ higher (or long-chain) fatty alcohol. The aliphatic groups of these fatty acids and fatty alcohols can be either straight-chain or branched chain and can be either saturated or unsaturated aliphatic groups, but from a practical viewpoint, it is preferred to choose one comprising a saturated aliphatic group.

As the $C_{18-34}$ higher fatty acid constituting the wax ester, there can be specifically mentioned ones contained in various natural waxes as a component, as they are or in a form of an ester, such as octadecanoic acid of $C_{18}$ (stearic acid), eicosanoic acid of $C_{20}$ (arachidic acid), docosanoic acid of $C_{22}$ (behenic acid), tetracosanoic acid of $C_{24}$ (lignoceric acid), hexacosanoic acid of $C_{26}$ (cerotic acid), octacosanoic acid of $C_{28}$ (montanic acid), triacontanoic acid of $C_{30}$ (melissic acid), dotriacontanoic acid of $C_{32}$ and tetratriacontanoic acid of $C_{34}$. In this connection, the names in the parentheses are common names.

The above fatty acids having an even number of atoms are generally easy to obtain, but fatty acids having an odd number of carbon atoms such as nonadecanoic acid of $C_{19}$ (non-adecylic acid) and tritriacontanoic acid of $C_{33}$ are not excluded so long as they can be obtained. Further, the aliphatic group can be branched, and for example, at least one of $C_{18-32}$ isoaliphatic acids (even number of carbon atoms), and $C_{19-33}$ anteisoaliphatic acids contained in the fatty acid composition of lanolin are included in the fatty acid constituting the wax ester in the invention.

Still further, fatty acids constituting these wax esters include compounds obtained by hydrogenating unsaturated fatty acids having the above carbon numbers, compounds obtained by etherifying hydroxy fatty acids corresponding to the above fatty acids with lower alkyl such as, for example, methyl, ethyl or propyl.

As more general examples of fatty acids constituting the wax esters of the invention, there can, for example, be mentioned behenic acid of $C_{22}$ constituting the wax esters of rapeseed wax, lignoceric acid of $C_{24}$ constituting the wax esters of rice bran oil wax (also contained in a large amount in carnauba wax), cerotic acid of $C_{26}$ constituting the wax esters of lanolin, montanic acid of $C_{28}$ constituting the wax esters of shellac wax, melissic acid of C30 and dotriacontanoic acid of $C_{32}$ constituting the wax esters of candelilla wax, and tetratriacontanoic acid of $C_{34}$ constituting the wax esters of shellac wax.

On the other hand, as to $C_{18-44}$ higher fatty alcohols constituting the wax esters, there can be mentioned, as general ones, for example, stearyl alcohol of C$_{18}$, eicosanol of $C_{20}$, docosanol of $C_{22}$, tetracosanol of $C_{24}$, hexacosanol of $C_{26}$, octacosanol of $C_{28}$, myricyl alcohol of $C_{30}$, laccerol of $C_{32}$, tetratriacontanol of $C_{34}$, etc., and futher tetratetracontanol of $C_{44}$. Further, branched alcohols, for example, those found mainly in lanolin such as 16-methyloctadecanol, 18-methylnonadecanol, 20-methylheneicosanol, 20-methyldocosanol, 22-methyltricosanol and 24-methylpentacosanol are also included. Further, the above higher fatty alcohols also include various alcohols obtained by chemical synthesis so long as they are alcohols having the above carbon numbers.

Thus, wax esters used in the invention include all of ones composed of any combination between one of $C_{18-34}$ higher fatty acids and one of $C_{18-44}$ higher fatty alcohols. Such wax esters can be mixtures of two or more.

Conveniently usable as such wax esters are, generally, ones composed of a higher fatty acid derived from natural wax components such as, for example, candelilla wax, carnauba wax, jojoba oil, lanolin, montan wax and rice wax, and a higher fatty alcohol derived from these waxes. Wax esters composed of a part derived from such a fatty acid and a part derived from such an alcohol can be esters synthesized from each fatty acid and each alcohol, or can be ones separated from the above waxes by extraction, etc.

Wax esters can be ones of any combination, and specific examples are $C_{20}$ fatty acid—$C_{20}$ alcohol, $C_{20}$ fatty acid—$C_{30}$ alcohol, $C_{24}$ fatty acid—$C_{28}$ alcohol, $C_{24}$ fatty acid—$C_{30}$ alcohol, $C_{24}$ fatty acid—$C_{32}$ alcohol, $C_{26}$ fatty acid—$C_{30}$ alcohol, $C_{26}$ fatty acid—$C_{32}$ alcohol, $C_{28}$ fatty acid—$C_{24}$ alcohol, $C_{28}$ fatty acid—$C_{28}$ alcohol, $C_{28}$ fatty acid—$C_{30}$ alcohol, $C_{30}$ fatty acid—$C_{28}$ alcohol, $C_{3}$ fatty acid—$C_{30}$ alcohol, $C_{30}$ fatty acid—$C_{32}$ alcohol, $C_{32}$ fatty acid—$C_{30}$ alcohol, $C_{32}$ fatty acid—$C_{32}$ alcohol, $C_{34}$ fatty acid—$C_{30}$ alcohol, $C_{34}$ fatty acid—$C_{32}$ alcohol, derived from candelilla wax, carnauba wax, jojoba oil or montan wax. Further, the esters by the above combinations include both of ones chemically synthesized and ones extracted from natural waxes.

As one obtained by chemical synthesis, included in the wax esters of the invention and commercially available, there can, for example, be mentioned CRODAMOL ODL (trade name, available from CRODA JAPAN Co., Ltd.) which is a reaction product of fatty acids of lanolin with 2-octyldodecyl alcohol.

Further, among the above natural waxes, those having a composition having no bad influence on the object of the invention can be used, as they are, together with the wax component of the invention. As to the composition having no bad influence, for example, since ones containing excessive hydroxy esters such as carnauba wax cause separation of the composition at the time of emulsification, and have a tendency to make its solidification difficult, caution is necessary for using them as such.

Amphoteric surface active agents usable in the invention include any ones so long as they are amphoteric surface active agents used in usual cosmetic bases, etc. As specific examples, there can be mentioned amidobetaine type amphoteric surface active agents represented by the following formula

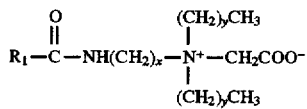

[Rebon 2000 (produced by Sanyo Kasei Co., Ltd.), Anon BDF (produced by Nippon Yushi Co., Ltd.), etc. are mentioned as commercial products], amidosulfobetaine type amphoteric surface active agents represented by the following formula

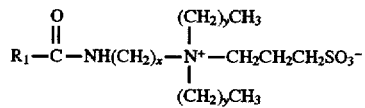

[Ronzain-CS (produced by Ronza Co.), Miradyne CBS (produced by Miranol Co.), etc. are mentioned as commercial products], betaine type amphoteric surface active agents represented by the following formula

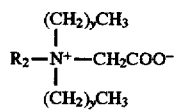

[Anon BL (produced by Nippon Yushi Co., Ltd.), Dehainton AB-30 (produced by Henkel Co.), etc. are mentioned as commercial products], sulfobetaine type amphoteric surface active agents represented by the following formula

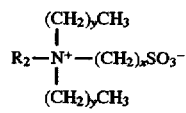

[Ronzain 12CS (produced by Ronza Co.), etc. are mentioned as commercial products], imidazolinium type amphoteric surface active agents represented by the following formula

[Ovazolin 662-N (produced by Toho Kagaku Co., Ltd.), Anon GLM (produced by Nippon Yushi Co., Ltd.), etc. are mentioned as commercial products], etc.

In the oil-in-water type cosmetic composition of the invention, based on the total weight of the composition, generally 0.1 to 10.0% by weight, preferably 1.0 to 5.0% by weight of the wax ester, and generally 0.5 to 10.0% by weight, preferably 0.5 to 1.5% by weight of the amphoteric surface active agent are contained. In this connection, in the wax ester, a hydroxy wax ester corresponding thereto can be contained in an amount of under 40% by weight based on the total weight of the wax ester. These wax ester and amphoteric surface active agent can be a mixture of two or more, respectively.

When the content of the wax ester in the composition of the invention is under 0.1% by weight, the composition becomes hard to solidify, and to the contrary, when the content goes beyond 10% by weight, there is a tendedcy that "being fresh-looking" and "refreshed feeling" of final products are decreased, and "stickiness" comes out. Further, when the content of the amphoteric surface active agent in the composition is under 0.5% by weight, emulsification comes to be difficut, and to the contrary, when the content goes beyond 10.0% by weight, there is a possibility that a problem on safety occurs on final products.

The composition of the invention contains, as another main component, a $C_{6-34}$ higher fatty acid. Such a fatty acid generally acts so as to heighten the stability in a solid state of the cosmetic composition of the invention. As specific examples of the fatty acid, there can be generally mentioned, besides the higher fatty acids exemplified as the constituents of the above wax esters, for example, hexanoic acid of $C_6$ (caproic acid), octanoic acid (caprylic acid) or 2-ethylhexanoic acid of $C_8$, decanoic acid of $C_{10}$ (capric acid), dodecanoic noic acid of $C_{12}$ (lauric acid), tetradecanoic acid of $C_{14}$ (myristic acid) and hexadecanoic acid of $C_{16}$ (palmitic acid), but fatty acids having odd carbon numbers such that the foregoing respective carbon numbers were incresed by one are not excluded. Further, when longer-chain fatty acids are used, hydroxy fatty acids corresponding thereto, for example 12-hydroxystearic acid can be used, and thus, fatty acids mentioned in the invention include hydroxy fatty acids.

There can be contained, in the oil-in-water type cosmetic composition of the invention, based on its total weight, generally, 0.1 to 10.0% by weight, preferably 0.1 to 2.0% by weight of the higher fatty acid. These higher fatty acids can be mixtures of two or more. Usually, when the higher fatty acid content is under 0.1% by weight, there is a case where emulsification stability is decreased, and to the contrary, when the content goes beyond 10.0% by weight, a possibility is heightened that a problem occurs on the safety in use final products.

Further, when the above higher fatty acid is contained, it is preferred that the mole ratio of the higher fatty acid/the amphoteric surface active agent is 1:15 to 1:0.8. When the mole ratio is under 1:15, there is case where emulsification is difficult, and when the mole ratio is above 1:0.8, there is case where an oil-in-water type emulsification composition cannot be formed.

In the composition of the invention, there can further be contained at least one of other later-described components which are compounded in cosmetics.

For example, as components serving for maintaining the stability of the solid state or heightening use feelings, there can be mentioned higher (long-chain) hydrocarbons contained in natural waxes and their equivalents on physical properties. As these, ones having a melting point above 50° C. are usually preferred. As specific examples thereof, there can, for example, be mentioned ones derived from beeswax, carnauba wax, candelilla wax or other animal or vegetable oils, such as, for example, pentacoxane ($C_{25}H_{52}$), heptacoxane ($C_{27}H_{56}$), hentriacontane ($C_{31}H_{64}$), dotriacontane ($C_{32}H_{66}$) and squalene ($C_{30}H_{50}$), or their hydrogenated products, for example, squalane which is a hydrogenated product of squalene.

These hydrocarbons can be added in an amount larger than the use amount of the wax ester, so long as the physical properties of the composition of the invention are not badly influenced, and for example, can be used even in an amount above almost twice the use amount by weight of the wax ester.

Therefore, there is also a case where it is convenient to use, for example, candelilla wax as it is in the composition of the invention.

There can further be contained, in the cosmetic composition of the invention, at least one of components for specific purposes, for example, for increasing the hardness, preventing cracks or heightening prevention of water volatilization, on final products, or for heightening specific efficacies at the time of use, such as, for example, prevention of ultraviolet rays, skin adsorptive properties, or actions, e.g. to hide pores in the skin or arrange the texture of the skin.

As specific examples of such components, there can be mentioned, silicone oils, ester oils (semisolid wax esters), higher alcohols, water soluble macromolecules, fatty acid esters of ethylene glycol or glycerol, titanium oxide and spherical powders.

As specific examples of the silicone oils, there can be mentioned trimethylsiloxysilicic acid—decastilcyclopentasiloxane, dimethylpolysiloxane, etc. These components can be contained, alone or as a mixture, in the solid cosmetic, generally in an amount of 0.1 to 40% by weight, based on the total weight of the solid cosmetic. As to their compounding method, these components can be contained in the oil phase at the later-described time of preparation (Examples). Addition of these components serves for increasing the hardness of the solid cosmetic.

As specific examples of the ester oils (semisolid wax esters), there can be mentioned esters having a part derived from a $C_{8-24}$ saturated or unsaturated higher fatty acid and a part derived from a $C_{14-24}$ saturated or unsaturated higher fatty alcohol. Fatty acids constituting the fatty acid part include the aforesaid saturated fatty acids having the corresponding carbon numbers or unsaturated fatty acids corresponding thereto, and also as to the alcohol part, alcohols are included having as the constituents straight-chain or branched chain or saturated or unsaturated long-chain hydrocarbons. All fatty acid esters composed of these fatty acid parts and alcohol parts can be used. Their use amount is generally 0.01 to 3.0% by weight, based on the total weight of the solid cosmetic, and as to their compounding method, they are usually added to the oil phase at the time of preparation. Addition of these components serves for crack prevention of the solid cosmetic.

As specific examples of the higher alcohols, there can be mentioned $C_{16-22}$ saturated fatty alcohols and $C_{16-22}$ saturated fatty ether—fatty alcohols. More specifically, there can be mentioned cetyl alcohol of $C_{16}$, stearyl alcohol of $C_{18}$, behenyl alcohol of $C_{22}$, batyl alcohol of $C_{18}$-O-$C_{3}$-, etc. As to their addition method, they are usually added to and dissolved in the above oil phase under heating. Their use amount is generally 0.005 to 2.0% by weight, based on the total weight of the solid cosmetic. These components can be used also alone or as a mixture, and usually serve for prevention of water volatilization from the cosmetic.

As specific examples of the water soluble macromolecules, there can be mentioned hydroxyethylcellulose, hyaluronic acid, high polymerization polyethylene glycol, xanthane gum, poly(meth)acrylic acid, methylcellulose, polyvinyl alcohol, dextran sulfate, chondroitin sulfate, polyvinylpyrrolidone and gum arabic, and salts of them with an alkali metal such as sodium or potassium in the case where they can be made into salts, etc. When one of them or a mixture of two or more are contained in the solid cosmetic in an amount of 0.001 to 3.0% by weight, based on the total weight of the solid cosmetic, they serve for prevention of water volatilization from the solid cosmetic. As to their compounding method, they are usually added to the aqueous phase at the time of preparation of the cosmetic.

As specific examples of the fatty acid esters of ethylene glycol or glycerol, there can be mentioned ethylene glycol diesters of the aforesaid $C_{18-30}$ saturated fatty acids and triglycerides of the $C_{18-30}$ saturated fatty acids. Particularly, it is preferred to use the former, and their use amount can be 0.001 to 5% by weight based on the total weight of the solid cosmetic, and in some case, part of the aforesaid wax ester can be substituted therefor. As to their compounding method, they are added to the above oil phase, and dissolved therein with heating to about 80° C. Addition of these components usually serve for heightening the hardness of the solid cosmetic of the invention.

As specific examples of the titanium oxide, there can be mentioned ultrafine, platy and needle titanium oxides, and, usually, one or a mixture of two or more of titanium oxides of these shapes are used. Their use amount can be, usually, 0.1 to 20% by weight based on the total weight of the solid cosmetic. As to their compounding method, they are mixed with other components by incorporating them in the general powder part at the time of preparation of the cosmetic. Addition of these components serves for heightening ultraviolet ray prevention action, although, thereby, there is a possibility that the hardness of the solid cosmetic is lowered within an allowable range.

As specific examples of the spherical powders, there can be mentioned spherical silica, spherical nylon powders, spherical alkyl polyacrylates, crosslinked polystyrene—squalane mixed powders, cellulose powder, silicic anhydride powder and methylsiloxane reticular polymer powder. At least one of them can be contained generally in an amount of 0.005 to 20% by weight based on the total weight of the solid cosmetic. Addition of these components serves, at the time of use of the solid cosmetic, at least for hiding pores on the skin and arranging the texture of the skin, or improving the adhesive properties of sebum.

Other components compoundable in cosmetics can be contained in the oil-in-water type cosmetic composition or solid cosmetic of the invention. These are, for example, oils, humectants, dispersants, powders, antiseptics, perfumes, medicaments, thickeners, coloring matters, pigments, etc. other than those mentioned above.

According to the invention, the resultant oil-in-water type cosmetic composition of the invention or solid cosmetic maintains a stable solid state, and in spite of a solid state, when applied on the skin, has the same "being fresh-looking", "refreshed feeling" and "being free of stickiness" as in oil-in-water type milky lotions and creams as use feelings, and, moreover, is excellent in storage stability.

The invention is further described below according to specific examples. All the compounding amounts in the following examples represent (weight/weight) %, unless otherwise defined.

EXAMPLE 1

Oil-in-water type emulsification compact

| Oil-in-water type emulsification compact (foundation) | | |
|---|---|---|
| (1) | Decamethylcyclopentasiloxane | 16.8 |
| (2) | Stearyl stearate | 5.0 |
| (3) | Red iron oxide | 1.0 |
| (4) | Yellow iron oxide | 3.0 |
| (5) | Black iron oxide | 0.2 |
| (6) | Titanium dioxide | 10.0 |
| (7) | Kaolin | 5.0 |
| (8) | Talc | 25.8 |

-continued

| Oil-in-water type emulsification compact (foundation) | | | |
|---|---|---|---|
| (9) | 1,3-Butylene glycol | 3.0 | |
| (10) | Methylparaben | 0.2 | |
| (11) | Deionized water | 25.0 | |
| (12) | 2-Alkyl-N-carboxymethyl-N-hydroxyethylimidazolinium betaine (purity 30%) | 5.0 | |

Preparation method (1) and (2) were stirred and melted at 70° C. to 80° C. to make an oil part, and (9) to (12) were stirred and dissolved at 70° C. to 80° C. to make an aqueous part. The aqueous part was added to the oil part to make an emulsion, and (3) to (8) previously stirred and mixed were mixed. The mixture was poured in a foundation middle plate, and cooled to obtain an emulsification compact. This compact was fresh-looking, and, in use, had refreshed feeling and was free of stickiness.

COMPARATIVE EXAMPLE 1

Oil-in-water type emulsification compact

| Oil-in-water type emulsification compact (foundation) | | |
|---|---|---|
| (1) | Decamethylcyclopentasiloxane | 16.8 |
| (2) | Stearyl hydroxystearate | 5.0 |
| (3) | Red iron oxide | 1.0 |
| (4) | Yellow iron oxide | 3.0 |
| (5) | Black iron oxide | 0.2 |
| (6) | Titanium dioxide | 10.0 |
| (7) | Kaolin | 5.0 |
| (8) | Talc | 25.8 |
| (9) | 1,3-Butylene glycol | 3.0 |
| (10) | Methylparaben | 0.2 |
| (11) | Deionized water | 25.0 |
| (12) | 2-Alkyl-N-carboxymethyl-N-hydroxyethylimidazolinium betaine (purity 30%) | 5.0 |

Preparation method

When preparation was made in the same manner as in Example 1, separation was caused at the time of emulsification, which was different from Example 1.

EXAMPLE 2

Oil-in-water type emulsification compact

| Oil-in-water type emulsification compact (foundation) | | |
|---|---|---|
| (1) | Octamethylcyclotetrasiloxane | 13.69 |
| (2) | Dimethylpolysiloxane (6 cs) | 5.0 |
| (3) | Product obtained by complete hydrogenation of jojoba oil | 0.07 |
| (4) | Stearyl lactate | 0.03 |
| (5) | Ceresine | 3.0 |
| (6) | Red iron oxide treated with dextrin fatty acid ester | 1.0 |
| (7) | Yellow iron oxide treated with dextrin fatty acid ester | 3.0 |
| (8) | Black iron oxide treated with dextrin fatty acid ester | 0.2 |
| (9) | Titanium dioxide treated with dextrin fatty acid ester | 10.0 |
| (10) | Sericite treated with dextrin fatty acid ester | 5.0 |
| (11) | Talc treated with dextrin fatty acid ester | 10.8 |
| (12) | Polymethyl methacrylate | 10.0 |

-continued

| Oil-in-water type emulsification compact (foundation) | | |
|---|---|---|
| | spherical powder | |
| (13) | 6,6-Nylon | 10.0 |
| (14) | Propylene glycol | 3.0 |
| (15) | Dynamite glycerol | 5.0 |
| (16) | Hyaluronic acid | 0.01 |
| (17) | Methylparaben | 0.1 |
| (18) | Deionized water | 15.0 |
| (19) | Coconut oil fatty acid amidopropylbetaine (purity 30%) | 5.0 |
| (20) | Perfume | 0.1 |

Preparation method

Powders were added to the oil part at 70° C. to 80° C., and the mixture was stirred and mixed at that temperature. The aqueous phase part was added to make an emulsion, and the emulsion was poured in a compact middle plate and cooled to obtain an emulsification compact. This compact was fresh-looking, and, in use, had refreshed feeling and was free of stickiness.

In this connection, each of the used dextrin fatty acid ester—treated powders was obtained by adding 95% by weight of a raw material powder to 5% by weight solution of a dextrin fatty acid ester in Isopar E (produced by Exxon Chemical Co.), stirring the mixture, removing the solvent, and drying and grinding the remaining matter.

EXAMPLE 3

Oil-in-water type emulsification stick foundation

| Oil-in-water type emulsification stick foundation | | |
|---|---|---|
| (1) | Decamethylcyclopentasiloxane | 8.9 |
| (2) | Squalane | 2.0 |
| (3) | Fluorocarbon | 0.2 |
| (4) | Octyl dodecyl lanolinate | 5.0 |
| (5) | Methyl hydroxystearate | 2.0 |
| (6) | Vaseline | 3.0 |
| (7) | Red iron oxide treated with silicone | 1.0 |
| (8) | Yellow iron oxide treated with silicone | 2.5 |
| (9) | Black iron oxide treated with silicone | 0.2 |
| (10) | Mica | 5.0 |
| (11) | Talc | 5.0 |
| (12) | 1,3-Butylene glycol | 5.0 |
| (13) | Dynamite glycerol | 10.0 |
| (14) | Methylparaben | 0.2 |
| (15) | Deionized water | 25.0 |
| (16) | Lauryl dimethylaminoacetic acid betaine (purity 40%) | 25.0 |

Preparation method

A mixture of all the components was prepared in the same manner as in Example 1, poured in a stick mold, and cooled to obtain an emulsification stick foundation. This stick was fresh-looking, and, in use, had refreshed feeling and was free of stickiness.

EXAMPLE 4

Oil-in-water type emulsification lipstick

| Oil-in-water type emulsification lipstick | | |
|---|---|---|
| (1) | Liquid paraffin | 60.89 |
| (2) | Castor oil | 0.5 |

-continued

Oil-in-water type emulsification lipstick

| | | |
|---|---|---|
| (3) | Dimethylpolysiloxane (100 cs) | 1.0 |
| (4) | Behenyl behenate | 3.0 |
| (5) | Octyl hydroxystearate | 1.0 |
| (6) | Diisostearyl malate | 1.0 |
| (7) | Red iron oxide | 0.3 |
| (8) | Yellow iron oxide | 1.0 |
| (9) | Red No. 204 | 0.7 |
| (10) | Red No. 202 | 0.01 |
| (11) | Carboxymethylcellulose sodium | 0.5 |
| (12) | 1,3-Butylene glycol | 3.0 |
| (13) | Sorbitol | 3.0 |
| (14) | Methylparaben | 0.1 |
| (15) | Deionized water | 20.0 |
| (16) | 2-Alkyl-N-carboxymethyl-N-hydroxyethylimidazolinium betaine (purity 30%) | 4.0 |

Preparation method

A mixture of all the components was prepared in the same manner as in Example 1, poured in a lipstick mold, and cooled to obtain an emulsification lipstick. This lipstick was fresh-looking, and, in use, had refreshed feeling and was free of stickiness.

EXAMPLES 5 AND 6 AND COMPARATIVE EXAMPLES 2 TO 6

Emulsification compositions were prepared in the same manner as in Example 1 using the compounding prescriptions shown in Tables 1 and 2. Among them, Example 5 is a water-in-oil type emulsification compact.

① Refreshed feeling, ② being fresh-looking, ③ being free of stickiness and ④ hardness were assessed on the obtained compositions, according to the following method. The results are shown, together with the results on the compositions of Examples 1 to 4 and Comparative example 1, in Table 3.

In table 3, "Preparation was impossible" means that emulsification was impossible because of occurence of seperation at the time of emulsification.

Assessment method

A use test was conducted by a panel of 20 experts, and the assessment results by them were averaged.

Assessment criterion

Grade 5: Very good
Grade 4: Good
Grade 3: A little good
Grade 2: Ordinary
Grade 1: Bad
Grade 0: Very bad Expression of assessment ++: Grade 4 or more
+: Grade 3 or more, under grade 4
±: Grade 2 or more, under grade 3
−: Grade 1 or more, under grade 2
—: Under grade 1

TABLE 1

| | | Example | | | Comparative example | |
|---|---|---|---|---|---|---|
| | | 1 | 5 | 6 | 1 | 2 |
| (1) | Decamethylcyclopentasiloxane | 16.8 | 16.8 | 16.8 | 16.8 | 16.8 |
| (2) | Stearyl stearate | 5.0 | 10.0 | 3.0 | — | 12.0 |
| (3) | Stearyl hydroxystearate | — | — | 2.0 | 5.0 | — |
| (4) | Microcrystalline wax | — | — | — | — | — |
| (5) | Red iron oxide | 1.0 | 1.0 | 1.0 | 1.0 | 1.0 |
| (6) | Yellow iron oxide | 3.0 | 3.0 | 3.0 | 3.0 | 3.0 |
| (7) | Black iron oxide | 0.2 | 0.2 | 0.2 | 0.2 | 0.2 |
| (8) | Titanium dioxide | 10.0 | 10.0 | 10.0 | 10.0 | 10.0 |
| (9) | Kaolin | 5.0 | 5.0 | 5.0 | 5.0 | 5.0 |
| (10) | Talc | 25.8 | 25.8 | 25.8 | 25.8 | 25.8 |
| (11) | 1,3-Butylene glycol | 3.0 | 3.0 | 3.0 | 3.0 | 3.0 |
| (12) | Methylparaben | 0.2 | 0.2 | 0.2 | 0.2 | 0.2 |
| (13) | Deionized water | 25.0 | 23.33 | 25.0 | 25.0 | 18.0 |
| (15) | 2-Alkyl-N-carboxymethyl-N-hydroxyethylimidazolinium betaine (30%) | 5.0 | 1.67 | 5.0 | 5.0 | 5.0 |

TABLE 2

| | | Comparative example | | | |
|---|---|---|---|---|---|
| | | 3 | 4 | 5 | 6 |
| (1) | Decamethylcyclopentasiloxane | 16.8 | 16.8 | 6.8 | 16.8 |
| (2) | Stearyl stearate | 0.05 | 10.0 | 5.0 | 2.0 |
| (3) | Stearyl hydroxystearate | — | — | — | 8.0 |
| (4) | Microcrystalline wax | — | — | — | — |
| (5) | Red iron oxide | 1.0 | 1.0 | 1.0 | 1.0 |
| (6) | Yellow iron oxide | 3.0 | 3.0 | 3.0 | 3.0 |
| (7) | Black iron oxide | 0.2 | 0.2 | 0.2 | 0.2 |
| (8) | Titanium dioxide | 10.0 | 10.0 | 10.0 | 10.0 |
| (9) | Kaolin | 5.0 | 5.0 | 5.0 | 5.0 |
| (10) | Talc | 25.8 | 25.8 | 25.8 | 25.8 |
| (11) | 1,3-Butylene glycol | 3.0 | 3.0 | 3.0 | 3.0 |
| (12) | Methylparaben | 0.2 | 0.2 | 0.2 | 0.2 |
| (13) | Deionized water | 29.95 | 24.0 | — | 20.0 |
| (15) | 2-Alkyl-N-carboxymethyl-N-hydroxyethylimidazolinium betaine (30%) | 5.0 | 1.0 | 40.0 | 5.0 |

TABLE 3

| | Example | | | | | | Comparative example | | | | | |
|---|---|---|---|---|---|---|---|---|---|---|---|---|
| | 1 | 2 | 3 | 4 | 5 | 6 | 1 | 2 | 3 | 4 | 5 | 6 |
| Refreshed feeling | ++ | ++ | + | ++ | + | ++ | (−)* | — | + | — | − | + |
| Being fresh-looking | ++ | ++ | + | ++ | + | ++ | (−) | — | + | — | − | + |
| Being free of stickiness | ++ | ++ | + | ++ | + | ++ | (−) | — | + | — | − | + |
| Hardness | ++ | + | + | + | + | + | (−) | + | — | + | + | — |

(−) Preparation was impossible

EXAMPLE 7

Oil-in-water type emulsification compact

| Oil-in-water type emulsification compact (foundation) | | |
|---|---|---|
| (1) | Decamethylcyclopentasiloxane | 15.8 |
| (2) | Candelilla wax | 5.0 |
| (3) | Stearic acid | 1.0 |
| (4) | Red iron oxide | 1.0 |
| (5) | Yellow iron oxide | 3.0 |
| (6) | Black iron oxide | 0.2 |
| (7) | Titanium dioxide | 10.0 |
| (8) | Kaolin | 5.0 |
| (9) | Talc | 25.8 |
| (10) | 1,3-Butylene glycol | 3.0 |
| (11) | Methylparaben | 0.2 |
| (12) | Deionized water | 25.0 |
| (13) | 2-Alkyl-N-carboxymethyl-N-hydroxyethylimidazolinium betaine (purity 30%) | 5.0 |

Preparation method (1) to (3) were stirred and melted at 70° C. to 80° C. to make an oil part, and (10) to (13) were stirred and dissolved at 70° C. to 80° C. to make an aqueous part. The aqueous part was added to the oil part to make an emulsion, and (4) to (9) previously stirred and mixed were mixed. The mixture was poured in a foundation middle plate, and cooled to obtain an oil-in-water type emulsification compact. This compact was fresh-looking, and, in use, had refreshed feeling and was free of stickiness. (higher fatty acid/amphoteric surface active agent (mole ratio)=0.86)

COMPARATIVE EXAMPLE 7

Oil-in-water type emulsification compact

| Oil-in-water type emulsification compact (foundation) | | |
|---|---|---|
| (1) | Decamethylcyclopentasiloxane | 15.8 |
| (2) | Carnauba wax | 5.0 |
| (3) | Stearic acid | 1.0 |
| (4) | Red iron oxide | 1.0 |
| (5) | Yellow iron oxide | 3.0 |
| (6) | Black iron oxide | 0.2 |
| (7) | Titanium dioxide | 10.0 |
| (8) | Kaolin | 5.0 |
| (9) | Talc | 25.8 |
| (10) | 1,3-Butylene glycol | 3.0 |
| (11) | Methylparaben | 0.2 |
| (12) | Deionized water | 25.0 |
| (13) | 2-Alkyl-N-carboxymethyl-N-hydroxyethylimidazolinium betaine (purity 30%) | 5.0 |

Preparation method

When preparation was made in the same manner as in Example 7, separation was caused at the time of emulsification, which was different from Example 7.

COMPARATIVE EXAMPLE 8

Oil-in-water type emulsification compact

| Oil-in-water type emulsification compact (foundation) | | |
|---|---|---|
| (1) | Decamethylcyclopentasiloxane | 15.8 |
| (2) | Microcrystalline wax | 5.0 |
| (3) | Stearic acid | 1.0 |
| (4) | Red iron oxide | 1.0 |
| (5) | Yellow iron oxide | 3.0 |
| (6) | Black iron oxide | 0.2 |
| (7) | Titanium dioxide | 10.0 |
| (8) | Kaolin | 5.0 |
| (9) | Talc | 25.8 |
| (10) | 1,3-Butylene glycol | 3.0 |
| (11) | Methylparaben | 0.2 |
| (12) | Deionized water | 25.0 |
| (13) | 2-Alkyl-N-carboxymethyl-N-hydroxyethylimidazolinium betaine (purity 30%) | 5.0 |

Preparation method

When preparation was made in the same manner as in Example 7, emulsion was possible, but no solid product was obtained, which was different from Example 7.

COMPARATIVE EXAMPLE 9

Oil-in-water type emulsification compact

| Oil-in-water type emulsification compact (foundation) | | |
|---|---|---|
| (1) | Decamethylcyclopentasiloxan | 15.8 |
| (2) | Candelilla wax | 5.0 |
| (3) | Stearic acid | 1.0 |
| (4) | Red iron oxide | 1.0 |
| (5) | Yellow iron oxide | 3.0 |
| (6) | Black iron oxide | 0.2 |
| (7) | Titanium dioxide | 10.0 |
| (8) | Kaolin | 5.0 |
| (9) | Talc | 25.8 |
| (10) | 1,3-Butylene glycol | 3.0 |
| (11) | Methylparaben | 0.2 |
| (12) | Deionized water | 28.5 |
| (13) | Polyoxyethylene (60 moles) - hardened castor oil | 1.5 |

Preparation method

When preparation was made in the same manner as in Example 7, emulsion was possible, but the viscosity of the resultant product was low, and separation occured with time lapse.

EXAMPLE 8

Oil-in-water type emulsification compact

| Oil-in-water type emulsification compact (foundation) | | |
|---|---|---|
| (1) | Octamethylcyclotetrasiloxane | 5.69 |
| (2) | Dimethylpolysiloxane (6 cs) | 5.0 |
| (3) | Candelilla wax | 0.1 |
| (4) | Ceresine | 3.0 |
| (5) | 12-Hydroxystearic acid | 8.0 |
| (6) | Red iron oxide treated with dextrin fatty acid ester | 1.0 |
| (7) | Yellow iron oxide treated with dextrin fatty acid ester | 3.0 |
| (8) | Black iron oxide treated with dextrin fatty acid ester | 0.2 |
| (9) | Titanium dioxide treated with dextrin fatty acid ester | 10.0 |
| (10) | Sericite treated with dextrin fatty acid ester | 5.0 |
| (11) | Talc treated with dextrin fatty acid ester | 10.8 |
| (12) | Polymethyl methacrylate spherical powder | 5.0 |
| (13) | 6,6-Nylon | 5.0 |
| (14) | Propylene glycol | 3.0 |

-continued

| Oil-in-water type emulsification compact (foundation) | |
|---|---|
| (15) Dynamite glycerol | 5.0 |
| (16) Hyaluronic acid | 0.01 |
| (17) Methylparaben | 0.1 |
| (18) Coconut oil fatty acid amidopropylbetaine (purity 30%) | 30.0 |
| (19) Perfume | 0.1 |

Preparation method

Powders were added to the oil part at 70° C. to 80° C., and the mixture was stirred and mixed at that temperature. The aqueous phase part was added to make an amulsion, and the emulsion was poured in a compact middle plate and cooled to obtain an emulsification compact. This compact was fresh-looking, and, in use, had refreshed feeling and was free of stickiness. (higher fatty acid/amphoteric surface active agent (mole ratio)=1.08)

In this connection, each of the used dextrin fatty acid ester—treated powders was obtained by adding 95% by weight of a raw material powder to 5% by weight solution of a dextrin fatty acid ester in Isopar E (produced by Exxon Chemical Co.), stirring the mixture, removing the solvent, and drying and grinding the remaining matter.

EXAMPLE 9

Oil-in-water type emulsification stick foundation

| Oil-in-water type emulsification stick foundation | |
|---|---|
| (1) Decamethylcyclopentasiloxane | 2.9 |
| (2) Squalane | 2.0 |
| (3) Fluorocarbon | 0.2 |
| (4) Candelilla wax | 10.0 |
| (5) Vaseline | 3.0 |
| (6) Isostearic acid | 3.0 |
| (7) Red iron oxide treated with silicone | 1.0 |
| (8) Yellow iron oxide treated with silicone | 2.5 |
| (9) Black iron oxide treated with silicone | 0.2 |
| (10) Mica | 5.0 |
| (11) Talc | 5.0 |
| (12) 1,3-Butylene glycol | 5.0 |
| (13) Dynamite glycerol | 10.0 |
| (14) Methylparaben | 0.2 |
| (15) Deionized water | 40.0 |
| (16) Lauryl dimethyl aminoacetic acid betaine (purity 40%) | 10.0 |

Preparation method

A mixture of all the components was prepared in the same manner as in Example 7, poured in a stick mold, and cooled to obtain an oil-in-water type emulsification stick foundation. This stick was fresh-looking, and, in use, had refreshed feeling and was free of stickiness. (higher fatty acid/amphoteric surface active agent (mole ratio)=0.72)

EXAMPLE 10

Oil-in-water type emulsification lipstick

| Oil-in-water type emulsification lipstick | |
|---|---|
| (1) Liquid paraffin | 60.69 |
| (2) Castor oil | 0.5 |
| (3) Dimethylpolysiloxane (100 cs) | 1.0 |
| (4) Candelilla wax | 3.0 |
| (5) Carnauba wax | 1.0 |

| Oil-in-water type emulsification lipstick | |
|---|---|
| (6) 12-Hydroxystearic acid | 0.1 |
| (7) Olein | 0.1 |
| (8) Diisostearyl malate | 1.0 |
| (9) Red iron oxide | 0.3 |
| (10) Yellow iron oxide | 1.0 |
| (11) Red No. 204 | 0.7 |
| (12) Red No. 202 | 0.01 |
| (13) Carboxymethylcellulose sodium | 0.5 |
| (14) 1,3-Butylene glycol | 3.0 |
| (15) Sorbitol | 3.0 |
| (16) Methylparaben | 0.1 |
| (17) Deionized water | 20.0 |
| (18) 2-Alkyl-N-carboxymethyl-N-hydroxyethylimidazolinium betaine (purity 30%) | 4.0 |

Preparation method

A mixture of all the components was prepared in the same manner as in Example 7, poured in a lipstick mold, and cooled to obtain an oil-in-water type emulsification lipstick. This lipstick was fresh-looking, and, in use, had refreshed feeling and was free of stickiness. (higher fatty acid/amphoteric surface active agent (mole ratio)=0.10)

EXAMPLES 11 TO 17 AND COMPARATIVE EXAMPLES 10 TO 15

Oil-in-water type emulsification compositions were prepared in the same manner as in Example 7 using the compounding prescriptions shown in Tables 4 to 7. In the tables, the prescriptions of Example 7 and Comparative examples 7 to 9 were also listed for reference.

① Refreshed feeling, ② being fresh-looking, ③ being free of stickiness and ④ hardness were assessed on the obtained compositions, in the same manner as in Examples 5 and 6 and Comparative examples 2 to 6. The results are shown, together with the results on the compositions of Examples 7 to 10 and Comparative examples 7 to 9, in Tables 8 and 9. The assesment was conducted according to the above-mentioned assessment method and assessment criterion.

TABLE 4

| | | Example | | | | |
|---|---|---|---|---|---|---|
| | | 7 | 11 | 12 | 13 | 14 |
| (1) | Decamethylcyclopenta-siloxane | 15.8 | 12.5 | 17.2 | 15.8 | 15.8 |
| (2) | Candelilla wax | 5.0 | 5.0 | 5.0 | 5.0 | 5.0 |
| (3) | Stearic acid | 1.0 | 1.0 | 0.3 | 1.0 | 0.4 |
| (4) | 12-Hydroxystearic acid | — | — | — | — | — |
| (5) | Red iron oxide | 1.0 | 1.0 | 1.0 | 1.0 | 1.0 |
| (6) | Yellow iron oxide | 3.0 | 3.0 | 3.0 | 3.0 | 3.0 |
| (7) | Black iron oxide | 0.2 | 0.2 | 0.2 | 0.2 | 0.2 |
| (8) | Titanium dioxide | 10.0 | 10.0 | 10.0 | 10.0 | 10.0 |
| (9) | Kaolin | 5.0 | 5.0 | 5.0 | 5.0 | 5.0 |
| (10) | Talc | 25.8 | 25.8 | 25.8 | 25.8 | 25.8 |
| (11) | 1,3-Butylene glycol | 3.0 | 3.0 | 3.0 | 3.0 | 3.0 |
| (12) | Methylparaben | 0.2 | 0.2 | 0.2 | 0.2 | 0.2 |
| (13) | Deionized water | 25.0 | — | 27.63 | 26.57 | 4.74 |
| (14) | 2-Alkyl-N-carboxymethyl-N-hydroxyethylimidazolinium betaine (30%) | 5.0 | 33.3 | 1.67 | 3.43 | 25.86 |
| (15) | Polyoxyethylene (60 moles) - hardened castor oil | — | — | — | — | — |
| Higher fatty acid/amphoteric surface active agent (mole ratio) | | 0.86 | 0.13 | 0.77 | 1.25 | 0.066 |

TABLE 5

| | | Example | | |
|---|---|---|---|---|
| | | 15 | 16 | 17 |
| (1) | Decamethylcyclopentasiloxane | 3.5 | 15.8 | 5.8 |
| (2) | Candelilla wax | 5.0 | 5.0 | 5.0 |
| (3) | Stearic acid | — | 0.7 | 0.3 |
| (4) | 12-Hydroxystearic acid | 10.0 | — | — |
| (5) | Red iron oxide | 1.0 | 1.0 | 1.0 |
| (6) | Yellow iron oxide | 3.0 | 3.0 | 3.0 |
| (7) | Black iron oxide | 0.2 | 0.2 | 0.2 |
| (8) | Titanium dioxide | 10.0 | 10.0 | 10.0 |
| (9) | Kaolin | 5.0 | 5.0 | 5.0 |
| (10) | Talc | 25.8 | 25.8 | 25.8 |
| (11) | 1,3-Butylene glycol | 3.0 | 3.0 | 3.0 |
| (12) | Methylparaben | 0.2 | 0.2 | 0.2 |
| (13) | Deionized water | — | 28.5 | 10.7 |
| (14) | 2-Alkyl-N-carboxymethyl-N-hydroxyethylimidazolinium betaine (30%) | 33.3 | 1.8 | 30.0 |
| (15) | Polyoxyethylene (60 moles) - hardened castor oil | — | — | — |
| Higher fatty acid/amphoteric surface active agent (mole ratio) | | 1.22 | 1.67 | 0.04 |

TABLE 6

| | | Comparative example | | | | |
|---|---|---|---|---|---|---|
| | | 7 | 8 | 9 | 10 | 11 |
| (1) | Decamethylcyclopentasiloxane | 15.8 | 15.8 | 15.8 | 5.8 | 16.6 |
| (2) | Candelilla wax | — | — | 5.0 | 5.0 | 5.0 |
| (3) | Carnauba wax | 5.0 | — | — | — | — |
| (4) | Microcrystalline wax | — | 5.0 | — | — | — |
| (5) | Stearic acid | 1.0 | 1.0 | 1.0 | 1.0 | 0.2 |
| (6) | Red iron oxide | 1.0 | 1.0 | 1.0 | 1.0 | 1.0 |
| (7) | Yellow iron oxide | 3.0 | 3.0 | 3.0 | 3.0 | 3.0 |
| (8) | Black iron oxide | 0.2 | 0.2 | 0.2 | 0.2 | 0.2 |
| (9) | Titanium dioxide | 10.0 | 10.0 | 10.0 | 10.0 | 10.0 |
| (10) | Kaolin | 5.0 | 5.0 | 5.0 | 5.0 | 5.0 |
| (11) | Talc | 25.8 | 25.8 | 25.8 | 25.8 | 25.8 |
| (12) | 1,3-Butylene glycol | 3.0 | 3.0 | 3.0 | 3.0 | 3.0 |
| (13) | Methylparaben | 0.2 | 0.2 | 0.2 | 0.2 | 0.2 |
| (14) | Deionized water | 25.0 | 25.0 | 18.0 | — | 29.0 |
| (15) | 2-Alkyl-N-carboxymethyl-N-hydroxyethylimidazolinium betaine (30%) | 5.0 | 5.0 | — | 40.0 | 1.0 |
| (16) | Polyoxyethylene (60 moles) - hardened castor oil | — | — | 12.0 | — | — |
| Higher fatty acid/amphoteric surface active agent (mole ratio) | | 0.86 | 0.86 | 1.05 | 0.11 | 0.86 |

TABLE 7

| | | Comparative example | | | |
|---|---|---|---|---|---|
| | | 12 | 13 | 14 | 15 |
| (1) | Decamethylcyclopentasiloxane | 15.8 | 15.8 | 2.8 | 15.8 |
| (2) | Candelilla wax | 5.0 | 12.0 | 5.0 | 12.0 |
| (3) | Carnauba wax | — | — | — | — |
| (4) | Microcrystalline wax | — | — | — | — |
| (5) | Stearic acid | 0.05 | 0.05 | 11.0 | 1.0 |
| (6) | Red iron oxide | 1.0 | 1.0 | 1.0 | 1.0 |
| (7) | Yellow iron oxide | 3.0 | 3.0 | 3.0 | 3.0 |
| (8) | Black iron oxide | 0.2 | 0.2 | 0.2 | 0.2 |
| (9) | Titanium dioxide | 10.0 | 10.0 | 10.0 | 10.0 |
| (10) | Kaolin | 5.0 | 5.0 | 5.0 | 5.0 |
| (11) | Talc | 25.8 | 25.8 | 25.8 | 25.8 |
| (12) | 1,3-Butylene glycol | 3.0 | 3.0 | 3.0 | 3.0 |
| (13) | Methylparaben | 0.2 | 0.2 | 0.2 | 0.2 |
| (14) | Deionized water | 29.15 | 22.15 | — | 18.0 |
| (15) | 2-Alkyl-N-carboxymethyl-N-hydroxyethylimidazolinium betaine (30%) | 1.8 | 1.8 | 33.0 | 5.0 |
| (16) | Polyoxyethylene (60 moles) - hardened castor oil | — | — | — | — |
| Higher fatty acid/amphoteric surface active agent (mole ratio) | | 0.12 | 0.12 | 1.43 | 0.86 |

TABLE 8

| | Example | | | | | | | | | | |
|---|---|---|---|---|---|---|---|---|---|---|---|
| | 7 | 8 | 9 | 10 | 11 | 12 | 13 | 14 | 15 | 16 | 17 |
| Refreshed feeling | ++ | + | + | ++ | + | ++ | ++ | + | + | + | + |
| Being fresh-looking | + | + | + | + | + | ++ | ++ | + | + | + | + |
| Being free of stickiness | ++ | + | + | ++ | + | ++ | ++ | + | + | + | + |
| Hardness | ++ | + | + | ++ | + | + | ++ | + | ++ | ± | ± |

TABLE 9

| | Comparative example | | | | | | | | |
|---|---|---|---|---|---|---|---|---|---|
| | 7 | 8 | 9 | 10 | 11 | 12 | 13 | 14 | 15 |
| Refreshed feeling | (−)* | ++ | ++ | − | − | + | − | — | — |
| Being fresh-looking | (−) | ++ | ++ | ± | ± | + | − | — | — |
| Being free of stickiness | (−) | ++ | ++ | − | − | + | − | — | — |
| Hardness | (−) | — | — | + | — | — | − | + | + |

(−) Preparation was impossible

EXAMPLES 18 TO 27

Solid cosmetics wherein additional cosmetic components were added (Part 1)

These example are for demonstrating, in preparation of compositions comprising water, wax esters, amphoteric surface active agents and higher fats, the addition effects of other cosmetic components particularly added in the oil phases, i.e., silicone oils, ester oils (or semisolid wax esters), higher alcohols, and fatty acid esters of ethylene glycol or glycerol.

Compositions (Examples 18 to 27) were prepared according to the preparation process described in Example 7 except that part of decamethylcyclopentasiloxane in the composition described in Example 7 was replaced respectively with the components shown in Table 10.

The effects of addition to the compositions on hardness, cracks inhibition and water volatilization inhibition were assessed. The results are shown, together with the assessment results on the composition of Example 7, in Table 10. Methods for the assessments are as follows.

Measurement of hardness

20 Samples on each composition were measured for hardness according to the measurement conditions shown in the aforesaid description of "solid", using a penetrometer (Reometer) produced by FUDO KOGYO CO. The hardness of each composition is shown as the average value of the measured values.

Volatilization prevention effect

20 Samples on each composition were left alone in an open system at room temperature (25° C.) for about one hour, and then measured for the weight changes, respectively. The volatilization prevention effect of each composition is shown as the average value of the decrease rates in weight based on the original weights. Assessment was made according to the following criterion.

| Expression of assessment | Decrease rate (%) |
|---|---|
| +++ | Under 0.7% |
| ++ | From 0.7% to under 1.0% |
| + | From 1.0% to under 1.3% |
| ± | 1.3% or more |

Cracks inhibition effect

The surfaces of 20 samples on each composition were scraped, the resultant samples were left alone in an open system at room temperature (25° C.), a tendency for cracks to occur on the samples was observed with time lapse, and their average behavior is classified and assessed as follows.

| Expression of assessment | Tendency for cracks to occur |
|---|---|
| +++ | Extremely hard to form |
| ++ | Hard to form |
| + | There is a case where several small cracks are formed on the samples |
| ± | There is a case where small cracks are formed on the greater part of the samples | lutely no bad influence on the hardness and volatilization of the compositions.

The higher alcohols significantly heightens the volatilization prevention effect without having no bad influence on the hardness and cracks formability of the compositions.

EXAMPLES 28 TO 34

Solid cosmetics wherein additional cosmetic components were added (Part 2)

These examples demonstrate effects obtained when, in place of part of talc among the components of Example 7, another spherical powder was added.

Preparation of compositions was made according to the preparation process described in Example 7, except that part of talc in Example 7 was replaced with components shown in Table 11.

Hardness, skin pore hiding effect and stickiness prevention effect (being free of stickiness) by the above addition to each composition were assessed. As to the hardness and being free of stickiness, the results obtained by making assessment according to the above methods are shown together in Table 11.

The skin pore hiding effect was relatively assessed compared with the composition of Example 7, through a use test using a panel of 20 experts. The relative assessment results by the 20 members were averaged, and the averaged assessment was expressed in Table 11 according to the following criterion.

TABLE 10

| Example number | 7 | 18 | 19 | 20 | 21 | 22 | 23 | 24 | 25 | 26 | 27 |
|---|---|---|---|---|---|---|---|---|---|---|---|
| (Oil components) | | | | | | | | | | | |
| Decamethylcyclopentasiloxane | 15.8 | 13.8 | 15.3 | 15.3 | 15.3 | 15.3 | 15.6 | 15.6 | 15.6 | 15.6 | 13.8 |
| Trimethylsiloxysilicic acid | 0 | 2.0 | 0 | 0 | 0 | 0 | 0 | 0 | 0 | 0 | 0 |
| Cetyl 2-ethylhexanoate | 0 | 0 | 0.5 | 0 | 0 | 0 | 0 | 0 | 0 | 0 | 0 |
| Octyldodecyleruate | 0 | 0 | 0 | 0.5 | 0 | 0 | 0 | 0 | 0 | 0 | 0 |
| Jojoba oil | 0 | 0 | 0 | 0 | 0.5 | 0 | 0 | 0 | 0 | 0 | 0 |
| Lanolin fatty acid octyldodecyl | 0 | 0 | 0 | 0 | 0 | 0.5 | 0 | 0 | 0 | 0 | 0 |
| Deodorized cetanol (value) | 0 | 0 | 0 | 0 | 0 | 0 | 0.2 | 0 | 0 | 0 | 0 |
| Behenyl alcohol | 0 | 0 | 0 | 0 | 0 | 0 | 0 | 0.2 | 0 | 0 | 0 |
| Stearyl alcohol | 0 | 0 | 0 | 0 | 0 | 0 | 0 | 0 | 0.2 | 0 | 0 |
| Batyl alcohol | 0 | 0 | 0 | 0 | 0 | 0 | 0 | 0 | 0 | 0.2 | 0 |
| Ethylene glycol fatty acid ester* | 0 | 0 | 0 | 0 | 0 | 0 | 0 | 0 | 0 | 0 | 2.0 |
| (Assessment) | | | | | | | | | | | |
| Hardness | 91 | 58 | 55 | 49 | 46 | 70 | 63 | 85 | 46 | 107 | 73 |
| Chaps prevention effect | ± | + | + | ++ | ++ | ++ | + | ± | + | ± | ± |
| Volatilization prevention effect | ± | ± | ± | ± | ± | + | + | ++ | ++ | ± | ± |

*Ethylene glycol diester of higher fatty acids (trade name "Synchrowax FRL-C", available from Cloda Japan Co., Ltd.)

From Table 10, the addition effects of silicone oils, ester oils (or semisolid wax esters), higher alcohols, and fatty acid esters of ethylene glycol or glycerol as additional components can be summarized, for example as follows.

Addition of the silicone oils or the diesters heightens the hardness of the compositions, and facilitates taking a desired amount thereof using, for example a finger, a sponge, a puff or the like, without having no bad influence on cracks formability and volatilization of the compositions.

Addition of the ester oils significantly heightens the cracks prevention effect without having almost no or abso-

| Expression of assessment | Relative assessment |
|---|---|
| +++ | Remarkable improvement is observed* |
| ++ | Considerable improvement is observed |
| + | A little improvement is observed. |
| ± | Equal to the composition of Example 7 |

*Pores become inconspicuous

TABLE 11

| Example number | 28 | 29 | 30 | 31 | 32 | 33 | 34 |
|---|---|---|---|---|---|---|---|
| (Powder) | | | | | | | |
| Talc | 20.8 | 20.8 | 20.8 | 20.8 | 20.8 | 20.8 | 20.8 |
| Silicic anhydride[a] | 5 | 0 | 0 | 0 | 0 | 0 | 0 |
| Nylon powder[b] | 0 | 5 | 0 | 0 | 0 | 0 | 0 |
| Allan mixed powder of crosslinked polystyrene[c] | 0 | 0 | 5 | 0 | 0 | 0 | 0 |
| Alkyl polyacrylate[d] | 0 | 0 | 0 | 5 | 0 | 0 | 0 |
| Cellulose powder[e] | 0 | 0 | 0 | 0 | 5 | 0 | 0 |
| Methylsiloxane reticular polymer[f] | 0 | 0 | 0 | 0 | 0 | 5 | 0 |
| Silicone powder[g] | 0 | 0 | 0 | 0 | 0 | 0 | 5 |
| Hardness | 73 | 55 | 60 | 65 | 83 | 64 | 52 |
| Inconspicuousness of pores | +++ | ++ | ++ | ++ | ++ | ++ | ++ |
| Being free of stickiness | +++ | ++ | ++ | ++ | ++ | ++ | +++ |

Powders of a) to g) used were those of the following trade names (manufacturer or selling agency).

a) Spherical silica P-1500 (Shokubai Kasei Co., Ltd.)
b) Nylon SP-500 (TORAY INDUSTRIES INC.)
c) Finepearl 3000 SPQ (SUMITOMO CHEMICAL COMPANY, LIMITED)
d) Microsphere M306 (Ethylene glycol dimethacrylate) (Matsumoto Yushi Seiyaku Co., Ltd.)
e) Selroflo C-25 (Chisso Corporation)
f) Tospearl 145A (Toshiba Silicone Co., Ltd.)
g) Trefil E-506S (TORAY INDUSTRIES INC.)

It is seen from Table 11 that addition of the spherical powders makes the skin pores inconspicuous, and significantly improve stickiness (sebum adsorptive properties, etc.), without having no bad influence on other properties of the compositions, for example, hardness.

EXAMPLES 35 TO 38

Solid cosmetics wherein additional cosmetic components were added (Part 3)

These examples demonstrate effects obtained when the entire titanium dioxide of Example 7 was replaced with titanium oxide of various shapes.

Preparation of compositions was made according to the preparation process described in Example 7, except that titanium oxide of specific shapes shown in Table 12 was used in place of titanium dioxide of Example 7.

The obtained compositions were assessed for hardness, skin pore hiding effect, stickiness prevention effect and ultraviolet ray insulation effect. The results are shown together in Table 12.

As to the hardness, inconspicuousness of pores and being free of stickiness, assessment was made according to the above assessment criteria. The ultraviolet ray insulation effect [ultraviolet ray insulation factor (UV-CUT (SPF))] was relatively assessed by conducting a use test by a panel of 20 experts, and comparing the degree of sunburn with the case of no addition (Example 7) (in Example 7, the value of sunburn degree was 14) one hour after start of the test.

TABLE 12

| | Example number | | | |
|---|---|---|---|---|
| | 35 | 36 | 37 | 38 |
| Particulate titanium oxide | 10 | 0 | 0 | 0 |
| Fatty acid-treated needle titanium oxide | 0 | 10 | 0 | 0 |
| Needle titanium oxide | 0 | 0 | 10 | 0 |
| Needle titanium oxide (treated with fatty acid) partially containing platy titanium oxide | 0 | 0 | 0 | 10 |
| Hardness | 63 | 11 | 2 | 90 |
| Inconspicuousness of pores | + | + | + | + |
| Being free of stickiness | + | + | + | + |
| UV-CUT (SPF) | 18 | 17 | 19 | 20 |

It is seen from Table 12 that when titanium oxide of specific shapes was used in place of titanium dioxide, inconspicuousness of pores and being free of stickiness are a little improved, and in addition, ultraviolet ray insulation effect is significantly heightened, although there is a case where the hardness of the compositions are lowered.

EXAMPLES 39 TO 49

Solid cosmetics wherein additional cosmetic components were added (Part 4)

These examples demonstrate effects obtained when a water soluble macromolecule was added to the composition of Example 7 (the macromolecule was substituted for part of the deionized water).

Preparation of compositions was made according to the preparation process described in Example 7, except that each water soluble macromolecule shown in Table 13 was added to the aqueous part of Example 7.

The obtained compositions were assessed for hardness and volatilization prevention effect. The results are shown together in Table 13.

TABLE 13

| Example number | 39 | 40 | 41 | 42 | 43 | 44 | 45 | 46 | 47 | 48 | 49 |
|---|---|---|---|---|---|---|---|---|---|---|---|
| Deionized water | 24.9 | 24.9 | 24.9 | 24.9 | 24.9 | 24.9 | 24.9 | 24.9 | 24.9 | 24.9 | 24.9 |
| Hydroxyethylcellulose | 0.1 | 0 | 0 | 0 | 0 | 0 | 0 | 0 | 0 | 0 | 0 |
| Sodium hyaluronate | 0 | 0.1 | 0 | 0 | 0 | 0 | 0 | 0 | 0 | 0 | 0 |
| High polymerization polyethylene glycol | 0 | 0 | 0.1 | 0 | 0 | 0 | 0 | 0 | 0 | 0 | 0 |
| Xanthane gum | 0 | 0 | 0 | 0.1 | 0 | 0 | 0 | 0 | 0 | 0 | 0 |
| Carboxyvinyl polymer | 0 | 0 | 0 | 0 | 0.1 | 0 | 0 | 0 | 0 | 0 | 0 |
| Methycellulose | 0 | 0 | 0 | 0 | 0 | 0.1 | 0 | 0 | 0 | 0 | 0 |
| Polyvinyl alcohol | 0 | 0 | 0 | 0 | 0 | 0 | 0.1 | 0 | 0 | 0 | 0 |
| Quinsseed extract | 0 | 0 | 0 | 0 | 0 | 0 | 0 | 0.1 | 0 | 0 | 0 |
| Dextran sulfate Na | 0 | 0 | 0 | 0 | 0 | 0 | 0 | 0 | 0.1 | 0 | 0 |
| Chondroitin sulfate Na | 0 | 0 | 0 | 0 | 0 | 0 | 0 | 0 | 0 | 0.1 | 0 |
| Gum arabic | 0 | 0 | 0 | 0 | 0 | 0 | 0 | 0 | 0 | 0 | 0.1 |
| Hardness | 91 | 84 | 73 | 77 | 93 | 89 | 83 | 65 | 66 | 70 | 78 |
| Volatilization prevention effect | ++ | ++ | ± | ++ | ± | + | +++ | + | +++ | +++ | + |

It is seen from Table 13 that there is a case where addition of certain water soluble macromolecules significantly improves the volatilization prevention effect, and further serves for improving hardness.

Industrial Applicability

The oil-in-water type cosmetic composition or solid cosmetic of the invention is excellent, as it is, in use feelings to skin, and can be an intermediate composition for cosmetics or a final cosmetic product. Therefore, it has a high applicability in the cosmetic manufacturing industry.

We claim:

1. A cosmetic composition which is a solid oil-in-water cosmetic composition comprising water, a wax ester and at least one of other components compounded in cosmetics, and contains, based on the total weight of the composition,
   (A) 0.1 to 10.0% by weight of at least one wax ester having a part derived from $C_{18-34}$ higher fatty acid and a part derived from $C_{18-44}$ higher fatty alcohol, and
   (B) 0.5 to 10.0% by weight of at least one amphoteric surface active agent.

2. A cosmetic composition which is a solid oil-in-water cosmetic composition comprising water, a wax ester and at least one of other components compounded in cosmetics, and contains, based on the total weight of the composition,
   (A) 0.1 to 10.0% by weight of at least one wax ester having a part derived from $C_{18-34}$ higher fatty acid and a part derived from $C_{18-44}$ higher fatty alcohol,
   (B) 0.5 to 10.0% by weight of at least one amphoteric surface active agent, and
   (C) 0.1 to 2.0% by weight of at least one $C_{6-34}$ higher fatty acid.

3. The composition according to claim 2 wherein the mole ratio of the component (C) to the component (B) is 1:15 to 1:0.8.

4. The composition according to claim 1 or 2 wherein the component (A) is at least one wax ester having a part derived from $C_{26-34}$ higher fatty acid and a part derived from $C_{28-44}$ higher fatty alcohol.

5. The composition according to claim 1 or 2 wherein the component (A) is a wax ester derived from candelilla wax.

6. The composition according to claim 1 or 2 wherein the component (B) is at least one member selected from the group consisting of amidobetaine, amido-sulfobetaine type, betaine, sulfobetaine type, and imidazolinium amphoteric surface active agents.

7. A solid cosmetic which is an oil-in-water solid cosmetic comprising water, a wax ester and at least one of other components compounded in cosmetics, and contains, based on the total weight of the composition,
   (A) 0.1 to 10.0% by weight of at least one wax ester having a part derived from $C_{18-34}$ higher fatty acid and a part derived from $C_{18-44}$ higher fatty alcohol,
   (B) 0.5 to 10.0% by weight of at least one amphoteric surface active agent,
   (C) 0 to 10.0% by weight of at least one $C_{6-34}$ higher fatty acid, and
   (D) at least one member selected from the group consisting of a silicone oil, an ester oil (or a semi-solid wax ester), a higher alcohol, a water soluble macromolecule, a fatty acid ester of ethylene glycol or glycerol, titanium oxide and spherical powder.

8. The solid cosmetic according to claim 7 wherein the silicone oil is trimethylsiloxysilicic acid—decastilcyclopentasiloxane or dimethylpolysiloxane.

9. The solid cosmetic according to claim 7 wherein the ester oil (or the semisolid wax ester) is a component containing at least one of esters each having a part derived from a $C_{8-24}$ saturated or unsaturated higher fatty acid and a part derived from a $C_{14-24}$ saturated or unsaturated higher fatty alcohol.

10. The solid cosmetic according to claim 7 wherein the higher alcohol is a $C_{16-22}$ saturated fatty alcohol or a $C_{16-22}$ saturated fatty ether—fatty alcohol.

11. The solid cosmetic according to claim 7 wherein the water soluble macromolecule is composed of at least one member selected from the group consisting of hydroxyethylcellulose, hyaluronic acid, high polymerization polyethylene glycol, xanthane gum, poly(meth)acrylic acid, methylcellulose, polyvinyl alcohol, dextran sulfate, chondroitin sulfate, polyvinylpyrrolidone and gum arabic.

12. The solid cosmetic according to claim 7 wherein the fatty acid ester of ethylene glycol or glycerol is an ester which is at least one of an ethylene glycol diester of a $C_{18-30}$ saturated fatty acid and a triglyceride of a $C_{18-30}$ saturated fatty acid.

13. The solid cosmetic according to claim 7 wherein titanium oxide is a combination of two or more of ultrafine, platy and needle titanium oxides.

14. The solid cosmetic according to claim 7 wherein the spherical powder is at least one powder selected from the group consisting of spherical silica, spherical nylon powder, spherical alkyl polyacrylate, crosslinked polystyrene—squalane mixed powder, cellulose powder, silicic anhydride powder and methylsiloxane reticular polymer powder.

15. The composition according to claim 1 or 2 wherein the wax ester comprises a hydroxy wax ester in a positive amount up to 40% by weight based on the total weight of the wax ester.

16. The composition according to claim 15 which has a hardness of 7 or more as measured with a penetrometer and as determined by the formula:

$$\gamma \text{ (Hardness)} = \frac{G \times L}{I \times a} \quad (dyn/cm^2)$$

wherein,

G: Measured stress (gr)×980 dyn
L: Thickness of the sample (mm)
I: Compression distance (mm)
a: Cross section of the needle (cm$^2$)

under the following measurement conditions:

Negative load: 2 kg
Diameter of needle: 5.6 φ
Penetration speed: 2 cm/min
Penetration distance: 1 mm
Measurement temperature: 37° C.

17. The solid cosmetic according to claim 7 wherein the wax ester comprises a hydroxy wax ester in a positive amount up to 40% by weight based on the total weight of the wax ester.

18. The solid cosmetic according to claim 17 which has a hardness of 7 or more as measured with a penetrometer and as determined by the formula:

$$\gamma \text{ (Hardness)} = \frac{G \times L}{I \times a} \quad (dyn/cm^2)$$

wherein,

G: Measured stress (gr)×980 dyn
L: Thickness of the sample (mm)
I: Compression distance (mm)
a: Cross section of the needle (cm$^2$)

under the following measurement conditions:

Negative load: 2 kg
Diameter of needle: 5.6 φ
Penetration speed: 2 cm/min
Penetration distance: 1 mm
Measurement temperature: 37° C.

* * * * *